United States Patent [19]

Jackson

[11] Patent Number: 4,850,350
[45] Date of Patent: Jul. 25, 1989

[54] CLOSED SYSTEM COMBINED SUCTION AND VENTILATION DEVICES

[75] Inventor: Isaac S. Jackson, Greenwich, N.Y.

[73] Assignee: Sheridan Catheter Corp., Argyle, N.Y.

[21] Appl. No.: 941,744

[22] Filed: Dec. 15, 1986

Related U.S. Application Data

[63] Continuation-in-part of Ser. No. 878,074, Jun. 23, 1986, abandoned.

[51] Int. Cl.⁴ .............................................. A61N 16/00
[52] U.S. Cl. ................................ 128/207.16; 601/33; 601/35; 601/119; 601/171
[58] Field of Search ......... 128/200.26, 207.14–207.16, 128/656–658; 604/27, 30, 32, 33, 35, 45, 118, 119, 120, 121, 163, 167, 169, 171, 173, 246, 248, 249, 283; 251/95, 106, 147, 148, 149.10, 149.11, 149.15, 208, 209

[56] References Cited

U.S. PATENT DOCUMENTS

| | | | |
|---|---|---|---|
| 2,912,982 | 11/1959 | Baisky | 128/207.14 |
| 3,232,578 | 2/1966 | Cousins | 604/119 |
| 3,335,723 | 8/1967 | Waldnon, Jr. | 604/103 |
| 3,395,705 | 8/1968 | Hamilton | 604/119 |
| 3,757,771 | 9/1975 | Ruegg et al. | 604/163 |
| 3,834,388 | 9/1974 | Suver | 604/119 |
| 3,877,428 | 4/1975 | Seagle et al. | 604/248 |
| 3,894,540 | 7/1975 | Bonner, Jr. | 604/171 |
| 3,902,500 | 9/1975 | Dryden | 604/171 |
| 3,991,762 | 11/1976 | Radford | 604/119 |
| 4,022,219 | 5/1977 | Basta | 128/207.14 |
| 4,178,932 | 12/1979 | Ryder et al. | 604/118 |
| 4,212,300 | 7/1980 | Meals | 604/119 |
| 4,240,417 | 12/1980 | Holever | 128/203.12 |
| 4,270,778 | 6/1981 | Brownell | 604/283 |
| 4,291,691 | 9/1981 | Cabal et al. | 128/204.18 |
| 4,306,556 | 11/1981 | Gandi et al. | 128/207.18 |
| 4,351,328 | 9/1982 | Bodai | 128/200.16 |
| 4,356,823 | 11/1982 | Jackson | 604/119 |
| 4,416,273 | 11/1983 | Grimes | 604/283 |
| 4,515,592 | 5/1985 | Frankhoeser | 604/171 |
| 4,569,344 | 2/1986 | Palmer | 604/119 |
| 4,573,965 | 3/1986 | Russo | 604/35 |

FOREIGN PATENT DOCUMENTS 0029864 6/1981 European Pat. Off. ............ 604/167

*Primary Examiner*—Max Hindenburg
*Assistant Examiner*—K. M. Reichle
*Attorney, Agent, or Firm*—Burns, Doane, Swecker & Mathis

[57] ABSTRACT

Closed system, combined suction and ventilation medico-surgical tube devices include (1) a suction catheter, (2) a suction control valve positioned at the distal end of the system, (3) a multi-port coupling unit through which the catheter is fed for aspiration of a patient, (4) a flexible tubular sheath providing a sterility protective enclosure for the catheter fixed at its distal end to the proximal end of the coupling unit and (5) a sheath relief valve. The coupling units (4) have two separate members, one of which is fitted axially into the other so they may rotate relative to each other about their longitudinal axes to close and open access of the catheter from the sheath through the coupling unit into the patient. The suction control valves (2) have first and second substantially identical parts positioned together along a longitudinal side in sliding engagement with each other for movement between an open and a closed position of the valves. The sheath relief valves (5) serve to prevent air in the sheath from becoming contaminated during use of the assembly.

19 Claims, 4 Drawing Sheets

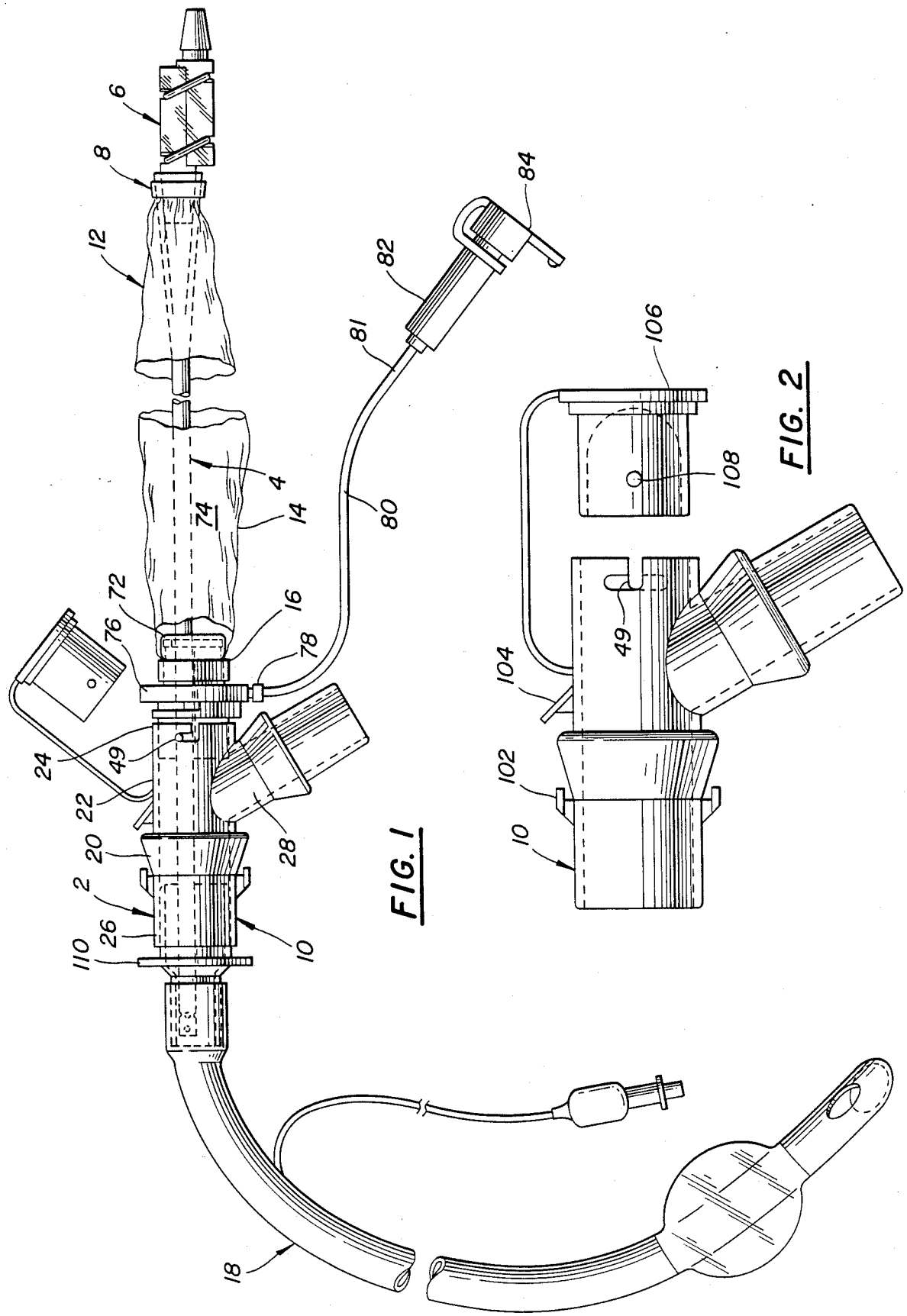

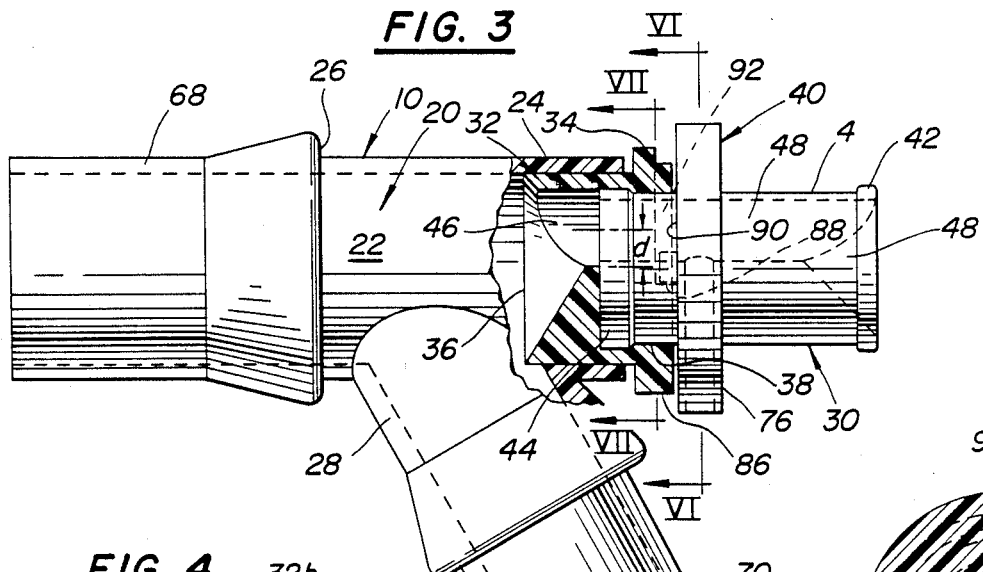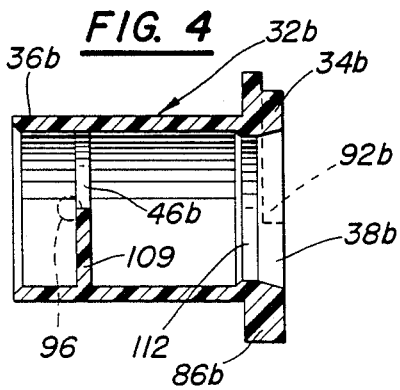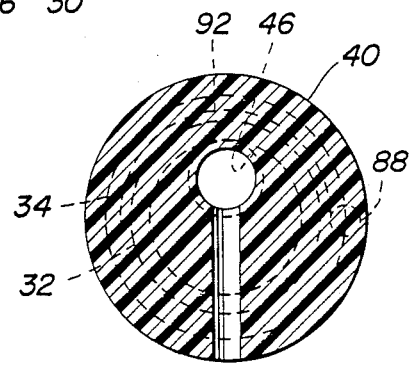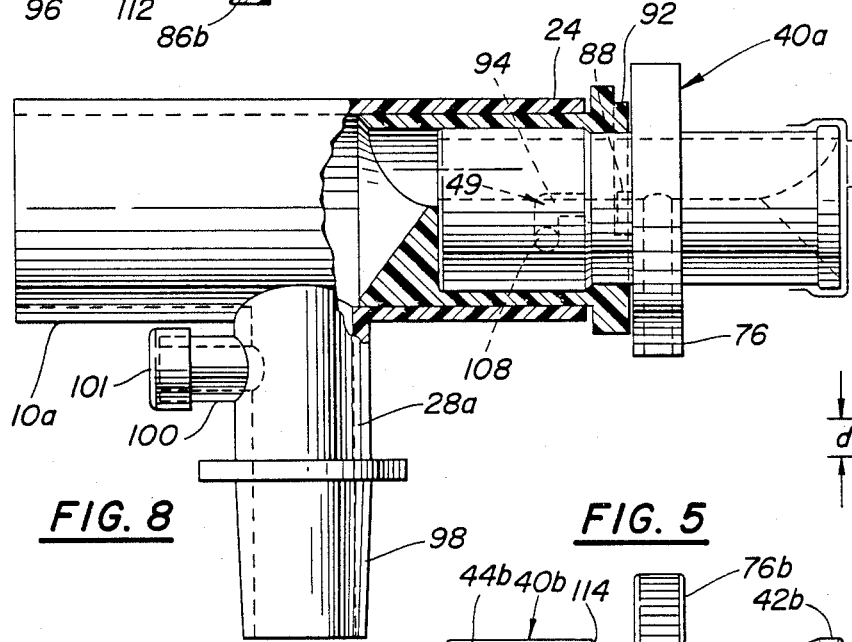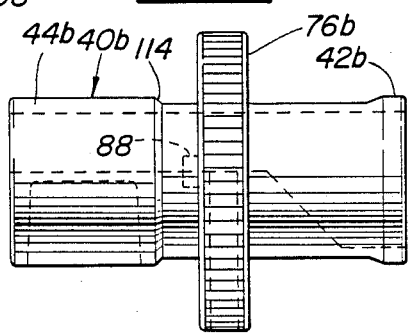

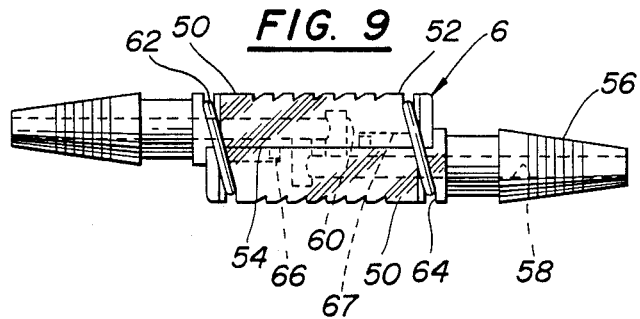
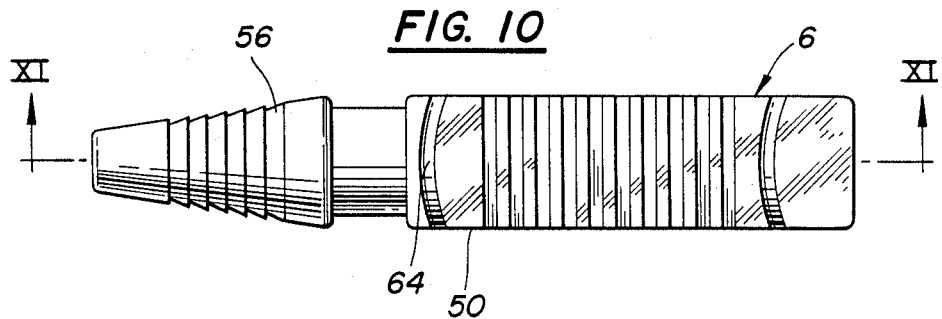
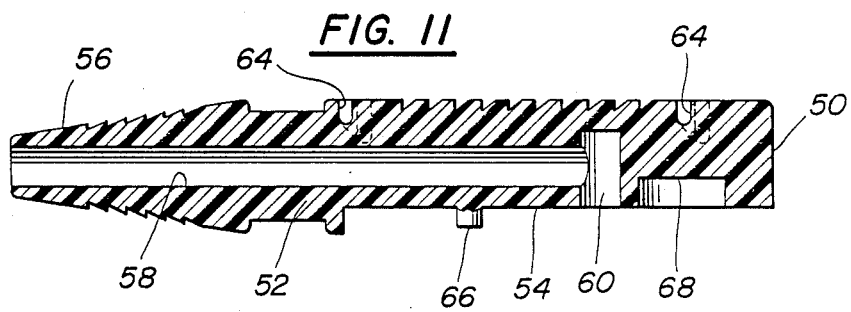
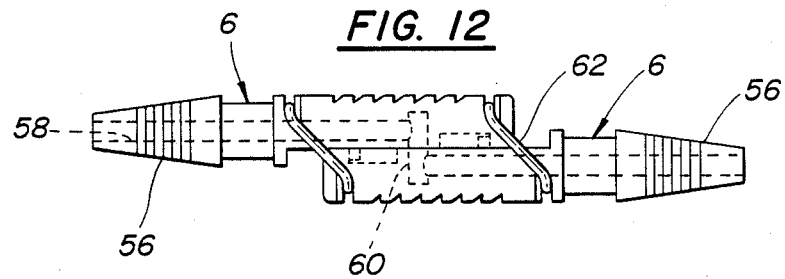
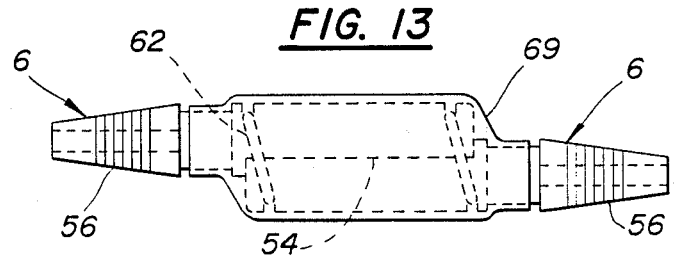

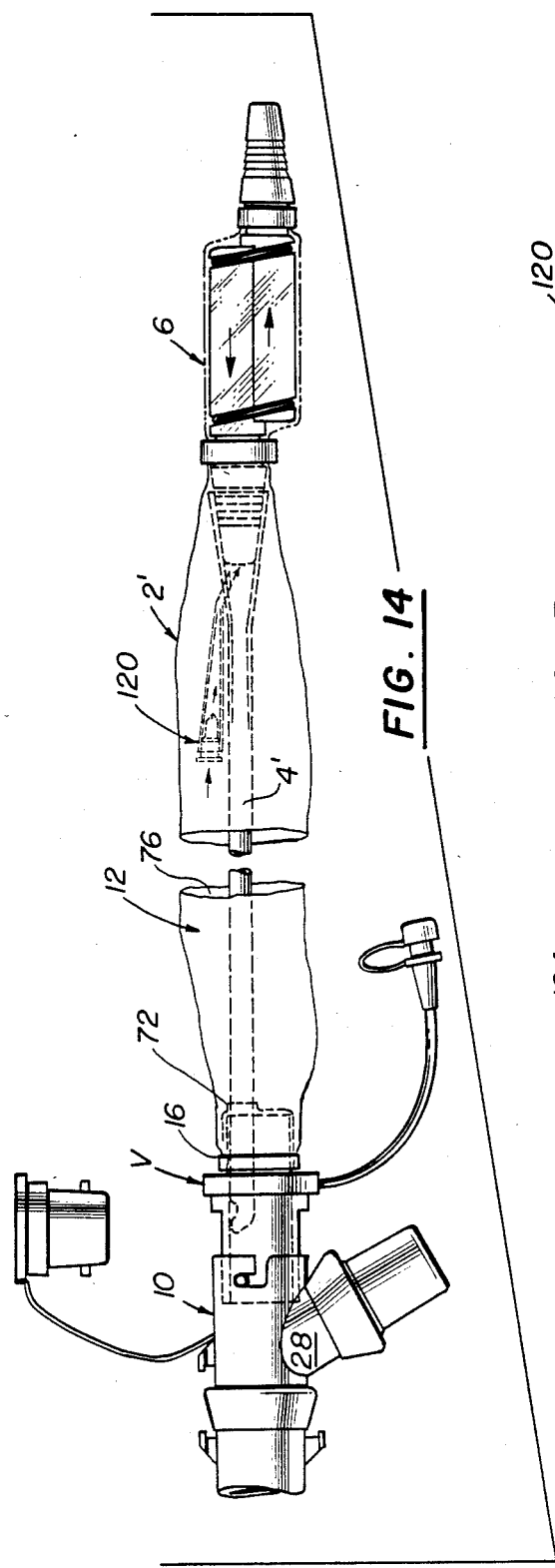
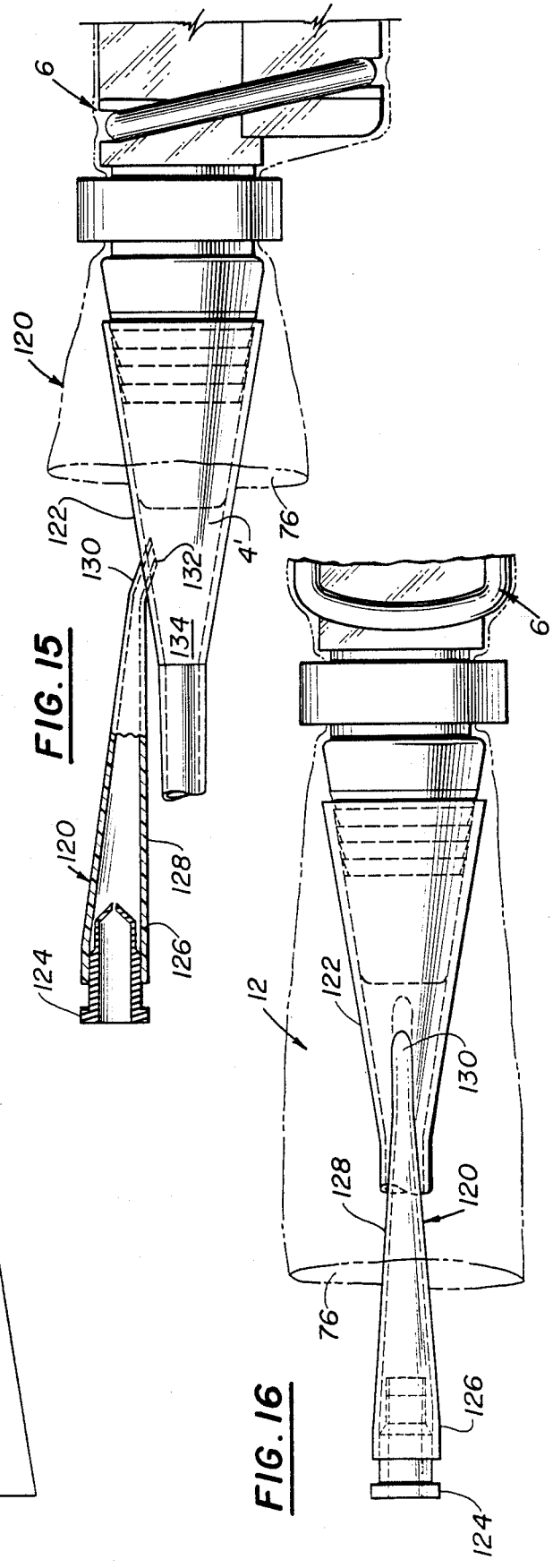
FIG. 14
FIG. 15
FIG. 16

CLOSED SYSTEM COMBINED SUCTION AND VENTILATION DEVICES

CROSS-REFERENCE TO RELATED APPLICATION

This is a continuation-in-part of application Ser. No. 878,074, filed June 23, 1986, now abandoned.

BACKGROUND OF THE INVENTION

1. Field of the Invention

This invention relates broadly to combination medico-surgical tube devices for use in both ventilating a patient via an in-dwelling tube and aspirating fluid from the patient via a catheter led intermittently into the patient through such tube. More particularly, it concerns such devices in which the suctioning catheter can be stored when not in use in isolation from the ambient within a protective sheath that forms a permanent part of a closed system.

2. Description of the Prior Art

A variety of systems are conventionally used to ventilate patients, e.g., to provide a patient with a flow of oxygenated air. One basic type system of major use employs an endotracheal tube, tracheostomy tube, or equivalent in-dwelling tube to couple the patient to external gas supply equipment.

In the use of such equipment, it is frequently necessary to remove fluid, e.g., mucus, blood, etc., that may accumulate in the patient's trachea or bronchi. In order to eliminate the need to disassemble the ventilation system to aspirate the patient, systems have been developed which permit a suctioning catheter to be inserted into the patient while the ventilation system remains in place as disclosed in U.S. patents:

| | |
|---|---|
| 2,912,982 | 4,291,691 |
| 4,022,219 | 4,300,550 |
| 4,240,417 | 4,351,328 |
| 4,499,548. | |

In the use of such combination devices, it was found desirable to be able to reuse a single catheter for repeated aspirations of the patient, rather then use a series of new catheters for multiple aspirations during a continuing ventilation procedure. However, this presents sterility problems, so the concept of using protective sheaths developed for repeated, sterile insertions of a single catheter through in-dewelling cannula (see U.S. Pat. Nos. 3,335,723; 3,757,771 and 3,894,540) was applied to the combination ventilation/aspiration devices as shown by U.S. Pat. Nos. 3,902,500 and 3,991,762.

The present invention advances the art of construction and using the combination devices by providing further improvements including unique coupling and valve units.

While special valves of a variety of designs have been developed for use in medico-surgical tube systems (see U.S. Pat. Nos. 4,193,406; 4,333,452; 4,342,315; 4,356,823 and 430,073), this invention provides yet another type of suction control valve especially suited for use in the combination ventilation/aspiration devices to which the invention pertains.

OBJECTS

A principal object of the invention is the provision of improved forms of closed system, combined suction and ventilation medico-surgical tube devices.

Further objects include the provision of:

1. Improved coupling units for connecting external ventilation equipment to an incubated patient which also provide a closed, sterile system for a suctioning catheter used in aspirating such patient.

2. Improved control valves for regulating the application of suction to the patient during aspiration in such combination ventilation/aspiration devices.

3. Means to insure that the catheter when in the protective sheath remains uncontaminated.

4. Improved combination ventilation/aspiration devices that contain a suction catheter with a closed assembly comprising a flexible, protective sleeve, a rotary on/off valve distal of the sleeve and an external on/off valve proximal of the sleeve.

5. Such devices in which the suction catheter can be fully retracted into the protective sheath and can be sealed off from the distal ventilation portion of the system whenever aspiration of the patient is not required.

6. Such devices in which the suction catheter and the protective sheath can be removed from the distal ventilation portion of the system for bronchoscopy.

7. Such devices that can be marketed as a combination of a single coupling unit and a plurality of sterile catheter/sleeve assemblies.

Other objects and further scope of applicability of the present invention will become apparent from the detailed description given hereinafter; it should be understood, however, that the detailed description, while indicating preferred embodiments of the invention, is given by way of illustration only, since various changes and modifications within the spirit and scope of the invention will become apparent to those skilled in the art from this detailed description.

SUMMARY OF THE INVENTION

The objects are accomplished, in part, in accordance with the invention by the provision of unique improvements in closed system, combined suction and ventilation medico-surgical tube devices that include a suction catheter, a suction control valve positioned in the distal end of the system, a multi-port coupling unit through which the catheter is fed for aspiration of a patient and a flexible tubular sheath providing a sterility protective enclosure for the catheter fixed at its distal end to the proximal end of the coupling unit.

The new improvements of the invention to the class of devices recited above include:

a multi-port coupling unit which comprises (A) a first member that has a longitudinal tubular element with a proximal end, a distal end and an integral side port, (B) a second member that includes a tubular distal part having a proximal end, a distal end and a major lumen extending along a first longitudinal axis distally of the proximal end, and a separate tubular proximal part with a cross-section approximately equal to the lumen of the distal part having a proximal end and distal end.

The distal end of the distal part is closed except for a hole substantially smaller in size than the lumen of the distal part with the center of the hole being offset a radial distance from the first longitudinal axis.

A second lumen approximating the size of the hole extends through the proximal part on a second longitudinal axis offset from the first longitudinal axis approximately equal to the aforesaid radial distance.

The distal end of the proximal part is fitted into the proximal end of the distal part, so the parts may rotate relative to each other about the first longitudinal axis, whereby the second lumen and the hole will coincide in one position of rotation of the proximal part in the distal part.

The distal part of the second member is connected to the proximal end of the first member.

The improved devices further comprise a suction control valve having first and second substantially identical parts positioned in sliding engagement with each other for movement between an open and a closed position of the valve.

Such valve parts have (1) a longitudinal body portion, (2) a flat surface extending along a side of the body portion on which the sliding engagement occurs, (3) a tapered connector element on one end of the body portion, (4) a lumen extending longitudinally through the connector element part way into the body portion, (5) limit means to fix the distance of relative movement between the identical parts from the open to the closed position, (6) a side port through the flat surface into the connector element lumen positioned so the port of the first identical part mates with the port of the second part when the parts are in the valve "open" position, and (7) elastic rings positioned about the identical parts biasing them into the valve "closed" position.

The new devices further include a one-way check valve located within the protective sheath to permit air within the sheath to be withdrawn from the system via the proximal end suction control valve.

BRIEF DESCRIPTION OF THE DRAWINGS

A more complete understanding of the invention may be had by reference to the accompanying drawings in which:

FIG. 1 is a fragmentary, plan view of one embodiment of a combination ventilation/aspiration medico-surgical tube device of the invention.

FIG. 2 is a enlarged, lateral view of one member of a coupling unit of the invention.

FIG. 3 is an enlarged, lateral view, partially in section, of a complete coupling unit of the invention.

FIG. 4 is a sectional view of one embodiment of a distal part of devices of the invention.

FIG. 5 is a lateral view of one embodiment of a proximal part of devices of the invention.

FIG. 6 is a sectional view taken on the line VI—VI of FIG. 3.

FIG. 7 is a sectional view taken on the line VII—VII of FIG. 3.

FIG. 8 is an enlarged, lateral view, partially in section, of another embodiment of a complete coupling unit of the invention.

FIG. 9 is a lateral view of a suction control valve for devices of the invention in a closed position.

FIG. 10 is an enlarged, plan view of the valve of FIG. 9.

FIG. 11 is a sectional view taken on the line XI—XI of FIG. 10.

FIG. 12 is a lateral view similar to FIG. 9, but with the valve in the open position.

FIG. 13 is a lateral view similar to FIG. 9, but with a protective, elastic boot in place enveloping the valve parts.

FIG. 14 is a lateral view of another embodiment of devices of the invention which includes a relief valve in the sheath portion of the device.

FIG. 15 is a fragmentary, enlarged lateral view of the relief valve portion of the device shown in FIG. 14.

FIG. 16 is a fragmentary, enlarged plan view of the relief valve portion of the device shown in FIG. 14.

DESCRIPTION OF THE PREFERRED EMBODIMENTS

Referring in detail to the drawings, in which identical parts are identically marked, the closed system, combined suction and ventilation medico-surgical tube device 2 includes a suction catheter 4, a suction control valve 6 positioned in the proximal end 8 of the device 2, a multiport coupling unit 10 through which the catheter is fed for aspiration of a patient and a flexible tubular sheath 12 providing a sterility protective enclosure for the catheter 4 fixed at its distal end 14 to the proximal end 16 of the coupling unit 10. The device 2 also includes an endotracheal tube 18.

The multi-port coupling unit 10 comprises a first, distal member 20 that has a longitudinal tubular element 22 with a proximal end 24, a distal end 26 and an integral side port 28. It also has a second, proximal member 30 that includes (A) a tubular distal part 32 having a proximal end 34, a distal end 36 and a major lumen 38 extending along a first longitudinal axis distally of the proximal end 34, and (B) a separate tubular proximal part 40 with a cross-section approximately equal to the lumen 38 having a proximal end 42 and distal end 44.

The distal end 36 of distal 32 part is closed except for a hole 46 substantially smaller in size than the lumen 38 with the center of the hole 46 being offset a radial distance d from the longitudinal axis of lumen 38.

A second lumen 48 approximating the size of the hole 46 extends through the proximal part 40 on a second longitudinal axis offset from the first longitudinal axis approximately equal to the aforesaid radial distance d. The proximal entrance to second lumen 48 is tapered to guide the distal end of catheter 4 when the catheter is fed in said device through connector unit 10 for aspiration of a patient (not shown).

The proximal part 40 is fitted into the proximal end 34 of the distal part 32, so the parts may rotate relative to each other about the first longitudinal axis, whereby the second lumen 48 and the hole 46 will coincide in one position of rotation of the proximal part 40 in the distal part 32.

The distal part 36 of the second member 30 is connected to the proximal end 24 of the first member 20 via lugs which cooperate with slat 49 to form a bayonet joint, as illustrated in FIG. 1.

The suction control valve 6 has first and second substantially identical parts 50 positioned in sliding engagement with each other for movement between an open and a closed position of the valve 6.

The valve parts 50 have a longitudinal body portion 52, a flat surface 54 extending along side 56 of the body portion 52 on which the sliding engagement between parts 50 occurs.

Parts 50 also include a tapered connector element 56 on one end of the body portion 52 and a lumen 58 extends longitudinally through the connector element part way into the body portion.

Also, there is a side port 60 through the flat surface 54 into the lumen 58 positioned so the port 60 of the first identical part 50 mates with the port 60 of the second part 50 when the parts are in the valve "open" position.

Elastic rings 62 are positioned in grooves 64 about the identical parts 50 biasing them into the valve "closed" position (see FIG. 7).

Limit means to fix the distance of relative movement between the identical parts 50 from the open to the closed position of the valve 6 includes a lug 66 extending from and a slot 67 in each flat surface 54 of the first and second parts 50. The valve parts 50 may be enclosed in a rubber glove (cover) 69.

In order to reduce the possibility of tube twisting problems occurring in the use of the device 2, the distal end 26 of the connector unit 10 is provided with a swivel connector 68 and the side port 28 has a similar swivel connector 70. The connectors 68 & 70 interlock with the respective end 26 and port 28 so as to be freely rotatable relative to one another.

A flexible diaphragm 72 covers the proximal end 42 of proximal part 40. There is a small hole in the diaphragm 72 through which the catheter 4 extends in sealing engagement therebetween to provide a substantially fluid-tight entrance for the catheter 4 from the protective enclosure 74 within the sheath 12 into the coupling unit 10.

The proximal part 40 has an integral flange 76 extending radially therefrom. A port 78 exits through the periphery of flange 76 and connects with the lumen 48. A flexible irrigation tube 80, which is attached to the port 78, has attached to its free end 81 a molded plastic connector end 82 that includes a one-way check valve (not shown) and a captured closure cap 84.

The proximal end 34 of distal part 32 has an integral flange 86 extending radially therefrom and adjacent faces of flanges 76 and 86 abut one another. Flange 76 includes a lug 88 extending from its adjacent face 90 and flange 86 includes a peripheral groove 92. The lug 88 in combination with groove 92 serve as means to limit degree of rotation of proximal part 40 in distal part 32.

In one embodiment, the proximal end 24 of first member 20 includes a bayonet lock grooves 49 and 94 and integral bayonet lugs 96 (108 in FIG. 8) extends from the side of distal part 32 into grooves 49 and 94 to lock distal part 32 into the first member 20.

In order to lock proximal part 40 into distal part 32, distal end 44 of part 40 has an O.D. slightly greater than the lumen 38. When parts 32 and 40 are pressed together for assembly, and interference fit occurs between end 44 and lumen 38. This produces a snap together fit, which when established, locks parts 32 and 40 together longitudinally, but permits them to rotate freely relative to one another.

FIG. 8 shows another embodiment of a connector unit 10a for the devices 2 of the invention. This unit 10a differs primarily from unit 10 in having a different form of side port 28a constructed with a male connector end 98 and an irrigation port 100, which may have a closure cap 101. Also, the part 40a is longer distally of the flange 76 than the part 40.

In either of the unit embodiments 10 & 10a, the side ports 28 & 28a serve for gas/oxygen input to the assembly 2 by connection to ventilation equipment (not shown) via the male 15.0 mm. connectors 70 or 98.

Regardless of the precise form of construction for the connector units 10, 10a, etc., they may be provided with integral tangs 102 and 104 around which elastic bands (not shown) may be stretched to lock parts in fixed position. Also, the units 10, etc. may be provided with captured closure caps 106 having bayonet lock pins 108 to function with the bayonet lock slot 49 to fix the cap 106 in connector unit 103, etc. when the second member 30 is removed from the unit 10 as illustrated in FIG. 2.

The proximal part 40 and distal part 32 may be molded of plastic, e.g., polypropylene, polyethylene, polycarbonate, polyvinyl chloride, A.B.S resin, etc. Such plastics will yield a few thousands of an inch when part 40 is pressed into part 32. When their molded interference portions have cleared each other, they become retention shoulders to lock the parts together in rotational engagement. Thus, the part 40 is made to dimensions which allow it to rotate freely in part 32 when fully assembled therein. A silicone grease can be applied as a lubricant and seal between parts 32 & 40. In one rotational position of part 40 relative to part 32, the hole 46 is aligned with the lumen 48 creating a passageway for the catheter 4. When part 40 is rotated, e.g., 180°, hole 46 and lumen 48 are no longer aligned so the portion of the assembly 2 distal of the part 40 is closed off from the sheath enclosure 74 and catheter 4. Thus, part 40 acting as a male part and distal part 32 as a female part together constitute a rotary valve V.

The devices 2 of the invention are supplied to the trade in sterile packages, typically with the catheter 4 fully withdrawn into the enclosure 74 and with the part 40 rotated so the valve comprising hole 46 and lumen 48 is closed shutting the sheath portion of the assembly off from the connector unit 10.

FIG. 1 shows the assembly 2 with the catheter 4 partially extended into the unit 10. When the catheter 4 is fully withdrawn into the sheath 12 and the part 40 is rotated to the "closed" position, the sterility of the catheter 4 is preserved while the device 2 is being connected to ventilation or other external equipment.

FIGS. 4 & 5 illustrate variations in dimensions and structural details in parts of the new devices of the invention. Thus, FIG. 4 illustrates a different embodiment of the distal part 32b as compared to part 32 of FIG. 3 while FIG. 5 shows a different embodiment of the proximal part 40b. compared to part 40 of FIG. 3.

In FIG. 4, the distal part 32b comprises proximal end 34b, distal end 36b and lumen 38b. The web 109 which transverses the lumen 38b adjacent the end 36b has a hole 46b through which the catheter will extend in use of the equipment. Part 32b also includes flange 86b, groove 92b and internal, annular, beveled lock flange 112.

In FIG. 5, the proximal part 40b comprises proximal end 42b, distal end 44b, ring flange 76b and rotation limit lug 88. It also includes a bevel 114 which functions with the flange 112 of part 32b to permit axially interlocking of parts 32b and 40b while providing for free relative rotation thereof. When separately molded part 40b is forced at its end 44b into lumen 38b of part 32b, their molded interference portions 112 and 114 finally clear each other to become retention shoulders to lock the parts together in rotational engagement. Thus, the part 40b is made to dimensions which allow it to rotate freely in part 32b when fully assembled therein.

The endotracheal tube 18 is usually not part of the packaged assembly 2. Normally, the doctor selects the endo tube in the operating room.

Use of the device 2 is easily performed. Upon removal from the sterile package (not shown), a breathing tube (not shown) from the ventilation equipment is attached to the male 15.0 mm connector 70 or 98. As taken from the package, the suction control valve 6, encased by the glove 69, has already been attached to the catheter 4. The proximal tapered end 56 must be inserted into a suction connecting tube (not shown).

The endo tube 15.0 mm adaptor 110 is attached to the female 15.0 mm end 26 of the connector unit 10. Then, the flange 76 is rotated to move the hole 46 in alignment with lumen 48, the unit 10 is held in one hand, while the catheter 4 is grasped in the other hand through the sleeve 12 and the catheter is moved through the unit 10 a few inches at a time.

To aspirate the patient, the control valve 6 is grasped between the thumb and forefinger of one hand with the tube (not shown) connecting it to a vacuum source (not shown) serving as a handle for the valve 6. To open the valve 6 and apply suction, forward pressure is applied to the upper part 50 of the valve 6. To stop suctioning, the pressure is released; the valve 6 is self-closing.

The unit 10 is continued to be held as the catheter is withdrawn from the patient back into the sheath 12. Suction is applied as often as necessary.

When the suctioning procedure has been completed, the catheter is flushed. For this, rotary valve part 40 is first closed and then a syringe of saline solution is inserted into the connector 82 of the irrigation tube 80. (The connector 82 is normally closed with the cap 84.) The syringe is held in one hand and the suction valve 6 is held in the other. Saline solution is introduced through the line and will enter the catheter at its distal end and exit its proximal end via the valve 6.

To complete the procedure, the suction valve 6 is closed, the syringe is removed from the fitting 82 and cap 84 is applied to it.

The device 2 can be left in place until the next suctioning, i.e., there is no ned to disconnect.

The device 2' is essentially like the devices 2 described above except for the presence of the relief valve means 120 fitted to the proximal end 122 of the suction catheter 4'.

The valve means 120 has a one-way check valve 124 fitted into the distal end 126 of a tapered connector member 128. The narrowed, proximal end 130 of the member 128 is cemented into a hole in the side of the end 122 of the catheter 4' so that the tip 132 of the end 130 exits in the interior 134 of the catheter 4'.

In use of the device 2', the sleeve 12 is not vented to ambient so that ambient air will not enter it as it is contracted and expanded when the catheter 4' is inserted into and withdrawn from the patient. Furthermore, there is no vent through the sleeve 12 to ambient which can permit contaminated air in the sleeve chamber 76 from getting out and possibly contaminating a nurse or other person operating the device during suctioning of a patient.

In the use of the devices 2 or 2', it is possible for the wiper/seal diaphragm 72 to allow small amounts of air from the patient's lungs to enter the chamber 76 as the catheter 4 or 4'inserted into and retracted from the patient. When this occurs, the entrapped air must be somehow expelled in order to permit the sleeve to contract on the next insertion of the catheter into the patient. In prior art devices, this has been accomplished by allowing the problem air accumulation to vent to ambient through a opening in the proximal portion of the sleeve, but this presents a contamination hazard as indicated above. The new device 2' prevent this from occurring.

Thus, when suction is applied through valve means 6, the sleeve chamber 76 is evacuated through the check valve 124. In addition to this, it is possible to vent any excess air out of the chamber 76 separate from the actual suction procedure by fully retracting the catheter 4' from the patient, next closing the rotary valve V thereby isolating the chamber 76 from the patient, and sliding the valve 6 to the ON position. Since the valve 6 is attached to a suctioning unit, any air in the chamber 76 will thereby be exhausted via valve 6.

THE EMBODIMENTS OF THE INVENTION IN WHICH AN EXCLUSIVE PROPERTY OR PRIVILEGE IS CLAIMED ARE DEFINED AS FOLLOWS:

1. In a closed system, combined suction and ventilation medico-surgical tube device that includes a suction catheter, a suction control valve positioned in the proximal end of said system and being connected to the suction catheter on one end and connectable to a source of suction on the other end, a multi-port coupling unit through which said catheter is fed for aspiration of a patient and a flexible tubular sheath providing a sterility protective enclosure for said catheter fixed at its distal end to the proximal end of said coupling unit and at its proximal end to the suction control valve, the improvements comprising:

a multi-port coupling unit which comprises:
    a first member that includes a longitudinal tubular element having a proximal end, a distal end for connection to a patient and an integral side port for connection to a ventilator,
    a second member that includes:
        a tubular distal part having a proximal end, a distal end and a major lumen extending along a first longitudinal axis at the center-line of the tubular distal part, and
        a separate tubular proximal part with a cross-section approximately equal to said lumen of said tubular distal part having a proximal end and distal end,
        said distal end of said distal part being closed except for a hole substantially smaller in size than said lumen, the center of said hole being offset a radial distance from said first longitudinal axis,
        a second lumen approximating the size of said hole extending through said proximal part on a second longitudinal axis offset from said first longitudinal axis approximately equal to said radial distance,
    said tubular proximal part of said second member being arranged to fit into said proximal end of said tubular distal part, so said parts may rotate relative to each other about said first longitudinal axis, whereby said second lumen and said hole will coincide in one position of rotation of said tubular proximal part in said tubular distal part,
    the tubular distal part of said second member being connected to the proximal end of said first member,
a suction control valve comprising:
    first and second substantially identical parts positioned in sliding engagement with each other for movement between an open and a closed position of said valve, said parts having:
        a longitudinal body portion,
        a flat surface extending along a side of said longitudinally extending body portion on which said sliding engagement occurs, a tapered connector element on a longitudinal end of said body portion, a lumen extending longitudinally through said connector element part way into said body portion, limit means to fix the distance of relative movement between said identical parts from said open to said closed position, a side port through said flat surface into said connector element lumen, said side port positioned so said port of said first identical part communicates with said port of said second identical part when said parts move in longitudinal directions into the open position, and elastic means positioned about said first and second substantially identical parts to connect the flat surfaces in engagement with each other and with the connector elements facing in opposite direction and for biasing said first and second substantially identical parts longitudinally towards each other into said closed position, and means fixing said distal end of said sheath to said coupling unit.

2. The device of claim 1 wherein said coupling unit includes a port through the side of said proximal part connecting to said second lumen.

3. The device of claim 2 wherein a flexible irrigation tube is attached to said port through the side of said proximal part.

4. The device of claim 2 wherein said proximal part has a first integral flange extending radially therefrom between the proximal and distal ends thereof.

5. The device of claim 4 wherein said port through the side of said proximal part exits through the periphery of said flange and a flexible irrigation tube is attached to said flange at said exit.

6. The device of claim 5 wherein said proximal end of said tubular distal part has a second integral flange extending radially therefrom and adjacent faces of said first and second flanges abut one another.

7. The device of claim 6 wherein said first flange includes a lug extending from its said adjacent face and said second flange includes a peripheral groove, said lug in combination with said groove serving as means to limit degree of rotation of said tubular proximal part in said tubular distal part.

8. The device of claim 6 wherein the free end of said irrigation tube is fitted with a molded connector unit that includes a one-way valve and captured closure cap.

9. The device of claim 1 wherein said coupling unit includes a tubular connector element rotatably attached to said distal end thereof and a tubular connector element rotatably attached to said side port thereof.

10. The device of claim 1 wherein said connection of said first member to said second member is via bayonet joint means for connecting the first member to the second member.

11. The device of claim 1 wherein a flexible diaphragm covers said tubular proximal end of said proximal part through which said catheter extends in sealing engagement therebetween to provide a substantially fluid-tight entrance for said catheter from said protective enclosure into said coupling unit.

12. The device of claim 1 wherein the I.D. of said second lumen approximates in size the O.D. of said catheter.

13. The device of claim 1 wherein said limit means of said suction control valve includes a lug extending from and a slot in each flat surface of said first and second substantially identical parts, respectively.

14. The device of claim 1 wherein the proximal entrance to said second lumen is tapered to guide the distal end of said catheter into said second lumen when the catheter is fed in said device for said aspiration of the patient.

15. The device of claim 1 wherein said integral side port has an irrigation port extending laterally therefrom.

16. In a closed system, combined suction and ventilation medico-surgical tube device that includes a suction catheter, a suction control valve positioned in the proximal end of said system and being connected to the suction catheter on one end and connectable to a source of suction on the other end, a multi-port coupling unit through which said catheter is fed for aspiration of a patient and a flexible tubular sheath providing a sterility protective enclosure for said catheter fixed at its distal end to the proximal end of said coupling unit and at its proximal end to the suction control valve, the improvements comprising:

a multi-port coupling unit which comprises:

a first member that includes a longitudinal tubular element having a proximal end, a distal end for connection to a patient and an integral side port for connection to a ventilator, a second member that includes:

a tubular distal part having a proximal end, a distal end and a major lumen extending along a first longitudinal axis at the center-line of the tubular distal part, and a separate tubular proximal part with a cross-section approximately equal to said lumen of said tubular distal part having a proximal end and distal end, said distal end of said distal part being closed except for a hole substantially smaller in size than said lumen, the center of said hole being offset a radial distance from said first longitudinal axis, a second lumen approximating the size of same hole extending through said proximal part on a second longitudinal axis offset from said fist longitudinal axis approximately equal to said radial distance, said proximal part of said second member being arranged to fit into said proximal end of said tubular distal part, so said parts may rotate relative to each other about said first longitudinal axis, whereby said second lumen and said hole will coincide in one position of rotation of said tubular proximal part in said distal part, the tubular distal part of said second member being connected to the proximal end of said first member, valve means that permits said sterility protective enclosure to exhaust into said suction catheter while preventing fluid within said suction catheter from entering into said sterility protective enclosure, and means fixing said distal end of said sheath to said coupling unit.

17. The closed system of claim 16 wherein said valve means include a check-valve connected to a tubular member which is in turn connected to the proximal end portion of said suction catheter for one-way fluid flow from said sterility protective enclosure through the proximal end portion of said suction catheter.

18. The closed system of claim 17 wherein said tubular member tapers downwardly from said check-valve toward said proximal end portion.

19. The closed system of claim 16 wherein said suction control valve comprises:
   first and second substantially identical parts positioned in sliding engagement with each other for movement between an open and a closed position of said valve, said part having:
   a longitudinal body portion,
   a flat surface extending along a side of said longitudinally extending body portion on which said sliding engagement occurs,
   a tapered connector element on a longitudinal end of said body portion,
   a lumen extending longitudinally through said connector element part way into said body portion,
   limit means to fix the distance of relative movement between said identical parts from said open to said closed position,
   a side port through said flat surface into said connector element lumen, said side port positioned so said port of said first identical part communicates with said port of said second identical part when said parts move in longitudinal directions into the open position, and
   elastic means positioned about said first and second substantially identical parts to connect the flat surfaces in engagement with each other and with the connector elements facing in opposite direction and for biasing said first and second substantially identical parts longitudinally towards each other into said closed position.

* * * * *